United States Patent
Jordan

(10) Patent No.: US 8,372,138 B2
(45) Date of Patent: Feb. 12, 2013

(54) SHAPE MEMORY POLYMERIC STENT

(75) Inventor: Gary Jordan, Litchfield, NH (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 914 days.

(21) Appl. No.: 12/136,147

(22) Filed: Jun. 10, 2008

(65) Prior Publication Data

US 2008/0312733 A1 Dec. 18, 2008

Related U.S. Application Data

(60) Provisional application No. 60/943,323, filed on Jun. 12, 2007.

(51) Int. Cl.
*A61F 2/06* (2006.01)
(52) U.S. Cl. .............................. 623/1.18
(58) Field of Classification Search ......... 623/1.1–1.54, 623/23.7
See application file for complete search history.

(56) References Cited

U.S. PATENT DOCUMENTS

| | | |
|---|---|---|
| 5,163,952 A | 11/1992 | Froix |
| 5,441,515 A | 8/1995 | Khosravi et al. |
| 5,603,722 A | 2/1997 | Phan et al. |
| 5,618,299 A | 4/1997 | Khosravi et al. |
| 5,670,161 A | 9/1997 | Healy et al. |
| 5,954,744 A | 9/1999 | Phan et al. |
| 5,964,744 A | 10/1999 | Balbierz et al. |
| 6,019,779 A * | 2/2000 | Thorud et al. ............ 606/198 |
| 6,364,904 B1 * | 4/2002 | Smith ......................... 623/1.22 |
| 6,887,266 B2 | 5/2005 | Williams et al. |
| 7,115,691 B2 | 10/2006 | Alvarado et al. |
| 7,118,592 B1 | 10/2006 | Dang et al. |
| 7,763,065 B2 * | 7/2010 | Schmid et al. ............ 623/1.15 |
| 2003/0216804 A1 | 11/2003 | DeBeer et al. |
| 2003/0220682 A1 | 11/2003 | Kujawski |
| 2004/0034405 A1 | 2/2004 | Dickson |
| 2004/0059408 A1 | 3/2004 | Alvarado et al. |
| 2004/0111111 A1 | 6/2004 | Lin |
| 2005/0049523 A1 | 3/2005 | Crank |
| 2005/0054950 A1 | 3/2005 | Parins |
| 2005/0054951 A1 | 3/2005 | Parins |
| 2005/0075625 A1 | 4/2005 | Dao et al. |
| 2006/0079955 A1 | 4/2006 | Brown |

* cited by examiner

*Primary Examiner* — Melanie Tyson
(74) *Attorney, Agent, or Firm* — Vidas, Arrett and Steinkraus

(57) ABSTRACT

An implantable, radially distensible stent includes a plurality of helically wound elongate members. The members include an overlapping portion having a longitudinal extent, opposed and convexly rounded sides defining a width of the members and opposed luminal and exterior surfaces. The members include shape memory polymer. The side of one elongate member slidingly overlaps the side of an adjacent elongate member to form a self-supporting wall structure of a stent. The stent wall is self-supporting without other support structure incorporated into or abutting the elongate members. Further, the shape memory polymer may include a biodegradable or bioabsorbable elements.

43 Claims, 10 Drawing Sheets

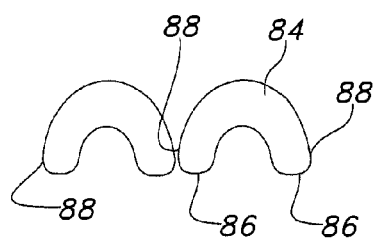
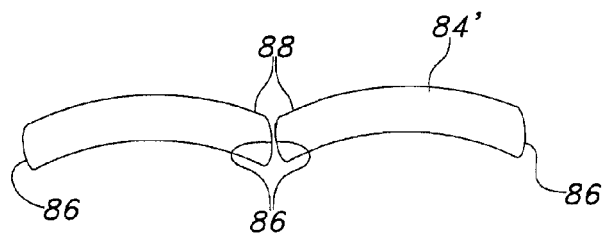
FIG. 14A  FIG. 14B
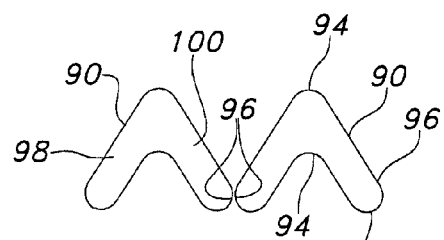
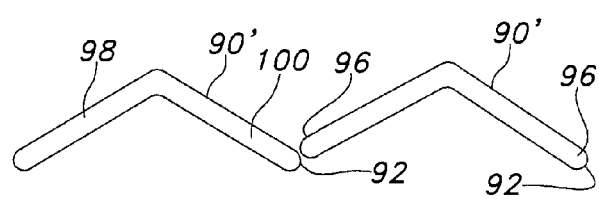
FIG. 15A  FIG. 15B
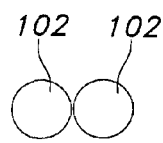
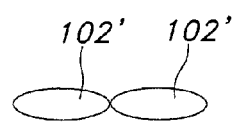
FIG. 16A  FIG. 16B

SHAPE MEMORY POLYMERIC STENT

CROSS-REFERENCE TO RELATED APPLICATIONS

This application claims the benefit of U.S. Provisional Application No. 60/943,323, filed Jun. 12, 2007, the contents of which are incorporated herein by reference.

FIELD OF THE INVENTION

This invention relates to a plastic stent. More particularly, the invention relates to a radially distensible stent made from a shape memory polymer and having a closed or substantially closed or fluid-tight stent wall.

BACKGROUND OF THE INVENTION

An intraluminary prosthesis is a medical device used in the treatment of diseased bodily lumens. One type of intraluminary prosthesis used in the repair and/or treatment of diseases in various body vessels is a stent. A stent is generally a longitudinal tubular device formed of biocompatible material which is useful to open and support various lumens in the body. For example, stents may be used in the bodily vessel, such as in the coronary or peripheral vasculature, esophagus, trachea, bronchi colon, biliary tract, urinary tract, prostate, brain, as well as in a variety of other applications in the body. These devices are implanted within the vessel to open and/or reinforce collapsing or partially occluded sections of the lumen.

Stents generally include an open lattice configuration. This configuration allows the stent to be inserted through curved vessels. Furthermore, this configuration allows the stent to be configured in a radially compressed state for intraluminary catheter implantation. Once properly positioned adjacent the damaged vessel, the stent is radially expanded so as to support and reinforce the vessel. Radial expansion of the stent may be accomplished by inflation of a balloon attached to the catheter or the stent may be of the self-expanding variety which will radially expand once deployed. Tubular shaped structures, which have been used as intraluminary vascular stents, have included helically wound coils which may have undulations or zig-zags therein, slotted stents, ring stents, braided stents and open mesh wire stents, to name a few. Super-elastic materials and metallic shape memory materials have also been used to form stents.

While stents are often made from metallic materials, the use of plastic stents is not uncommon, especially in non-vascular applications. For example, plastic stents have been used to treat malignant or benign strictures throughout the gastrointestinal tract because of, among other things, ease of placement and non-permanency of the stents. In the case of biliary applications, re-intervention of a plastic stent after three months is typical for malignant tumors where after the plastic stent is replaced with another plastic stent or perhaps a metallic stent. Benign strictures in biliary applications are often treated every three months with a plastic stent for up to about a year. In duodenal applications, a plastic stent is often placed as a bridge to surgery. In esophageal applications, a plastic stent may be placed as an adjunct treatment to radiation.

While plastic stents offer many advantages, a drawback of a typical plastic stent is its patency rate as compared to a metallic stent. A metallic stent generally has much larger radial force and a longer patency rate, especially when the stent is covered. Metal stents, however, have generally not been used in benign applications due to the difficulty of removing an implanted metallic stent.

In biliary applications, re-intervention may be required in about twenty-five percent of the time due to tumor in-growth through the open lattice portions of the implanted stent. Covering the stent, for example with a layer of silicone, may reduce the re-intervention due to tumor in-growth less than two percent of the time.

U.S. Pat. No. 5,603,722 to Phan et al describes a stent made from plastic, more particularly a shape memory polymer. The stent includes elongate strips of shape memory polymer overlapping wound to form a closed-wall stent structure in a contacted state of the stent. When the stent is expanded portions of the strip segments separate from each other to provide a stent with an open lattice structure. U.S. Pat. No. 5,163,952 to Froix describes a stent made from plastic, more particularly a shape memory polymer, which is in the shape of a coil or a solid-walled tubular cylinder. While the coil is a flexible structure, it has gaps into which tumor in-growth may occur. The solid-walled tubular cylinder may avoid the tumor in-growth concerns associated with open lattice stent structures, but such a stent is not highly flexible, making delivery and placement into curved lumens difficult.

Thus, there is a need for a plastic stent which has improved patency by reducing re-intervention rates due, for example, to tumor in-growth, while still being flexible so that it can used in curved lumens.

SUMMARY OF THE INVENTION

In one embodiment, the invention is directed to a plastic stent which has a closed or substantially closed wall structure to minimize tumor in-growth while still having sufficient flexibility to be used in curved lumens.

In one embodiment of the invention, an implantable, radially distensible stent is provided. The stent of this aspect of the invention includes a plurality of helically wound elongate members, the members including an overlapping portion having a longitudinal extent, opposed sides defining a width of the members and opposed luminal and exterior surfaces; the members including shape memory polymer; where the side of one elongate member slidingly overlaps the side of an adjacent elongate member to form a self-supporting wall structure of a stent. Desirably, one of the opposed sides of one elongate member slidingly overlaps one of the opposed sides of an adjacent elongate member to define the overlapping portion and to so form the self-supporting wall structure of the stent. The exterior surface of the elongate members forms an exterior portion of the wall structure of the stent, and the exterior surface of the elongated members may be a planar surface, a curved surface and combinations thereof. Desirably, the exterior surface of the elongated members is a curved surface. The luminal surface of the elongated members may further include a raised convexly arched, lobately shaped protuberance. The elongate members may be described as generally T-shaped members with rounded edges. Desirably, the stent wall is self-supporting without other support structure incorporated into or abutting the elongate members. Further desirably, the shape memory polymer may be a biodegradable or bioabsorbable polymer, in total or in part. To minimize in-growth, the elongate members are extruded, molded or cast members.

In another embodiment of the invention, an implantable stent is provided which consists essentially of a plurality of helically wound elongate members. Desirably, the elongate members are configured to minimize in-growth. The members may include an overlapping portion having a longitudinal extent, opposed sides defining a width of the members and opposed luminal and exterior surfaces. Further, the members are made from a material including shape memory polymer. The shape memory polymer may comprise biodegradable or bioabsorbable materials and/or elements. The side of one elongate member may slidingly overlap the side of an adjacent elongate member to form a self-supporting and closed or substantially closed wall structure of a stent. The stent is desirably self-supporting without other support structure incorporated into or abutting the elongate members. Desirably, one of the opposed sides of one elongate member slidingly overlaps one of the opposed sides of an adjacent elongate member to define the overlapping portion and to so form the self-supporting wall structure of the stent. The exterior surface of the elongate members form an exterior portion of the wall structure of the stent, and the exterior surface of the elongated member may be a curved surface, such as a convexly curved surface. The luminal surface of the elongated members may further include a raised convexly arched, lobately shaped protuberance.

In another embodiment of the invention, an implantable, radially distensible stent includes a helically wound elongate T-shaped member having a first upper traverse extent and a second perpendicularly projecting extent; where the first extent includes opposed and convexly rounded sides defining a width of the first extent and opposed luminal and exterior surfaces; where the second extent includes a convexly arched, lobately shaped protuberance; where the side of a portion of the first extent of the elongate member slidingly overlaps a portion of the luminal or exterior surface an adjacently juxtaposed portion of the elongate member to form a self-supporting wall structure of a stent. The stent member may include shape memory polymer, comprising a biodegradable or bioabsorbable shape memory polymer. Again, desirably, the self-supporting wall structure does not have an open lattice wall structure. The exterior surface of the first extent of the elongate member forms an exterior portion of the wall structure of the stent, and the exterior surface may be a curved surface, including a convexly curved surface. Again, the stent wall may be self-supporting without other support structure incorporated into or abutting the elongate member. Desirably, the shape memory polymer is biodegradable or bioabsorbable. The stent may further include a plurality of helically wound T-shaped members.

In another embodiment of the invention, a radially distensible stent is provided which includes a tubular wall having opposed open ends; where the tubular wall includes a plurality of and helically wound and overlapping elongate members included of shape memory polymer; where the stent is radially distensible between a radially contracted state and a radially expanded state; and where the tubular wall is a substantially closed wall without gaps between the helically wound members in the radially contracted and radially expanded states. The present invention, however, is not so limited, and the tubular wall may be somewhat or proximately a closed wall without substantial gaps between the helically wound members in the radially contracted and radially expanded states. The elongate tubular members are desirably non-textile members. Further, the elongate tubular members desirably include a plurality of curved surfaces.

These and other embodiments, objectives, aspects, features and advantages of this invention will become apparent from the following detailed description of illustrative embodiments thereof, which is to be read in connection with the accompanying drawings in which like reference characters refer to the same parts or elements throughout the different views. The drawings are not necessarily to scale, emphasis instead being placed upon illustrating the principles of the invention.

BRIEF DESCRIPTION OF THE DRAWINGS

FIG. 14A is a cross-sectional view of another embodiment of stent elements of FIGS. 1 and/or 2 having a convexly downward C-shape.

FIG. 14B is a cross-sectional view of the C-shaped elements of FIG. 14A after shape memory polymer extends to provide an elongated and less curved orientation of the stent elements.

FIG. 15A is a cross-sectional view of another embodiment of stent elements of FIGS. 1 and/or 2 having a convexly downward arched shape.

FIG. 15B is a cross-sectional view of the arched shaped elements of FIG. 15A after shape memory polymer extends to provide an elongated and less arched orientation of the stent elements.

FIG. 16A is a cross-sectional view of another embodiment of stent elements of FIGS. 1 and/or 2 having a round shape.

FIG. 16B is a cross-sectional view of the round-shaped elements of FIG. 16A after shape memory polymer extends to provide an elongated and oval orientation of the stent elements.

DETAILED DESCRIPTION OF THE INVENTION

The present invention relates to radially distensible stent having no or minimal gaps among its stent members, thereby minimizing the potential for tumor in-growth. The stent of the present invention has a fluid-tight or substantially fluid-tight stent wall without the need for a separate liner or cover, as is typically required where fluid-tight or continuous walls are desired for a stent with an open lattice structure. If a fluid-tight or continuous stent wall is not required, then the stent of the present invention could comprise a stent wall having any suitably sized gaps between the stent members to provide an open lattice stent wall.

Figure 1:
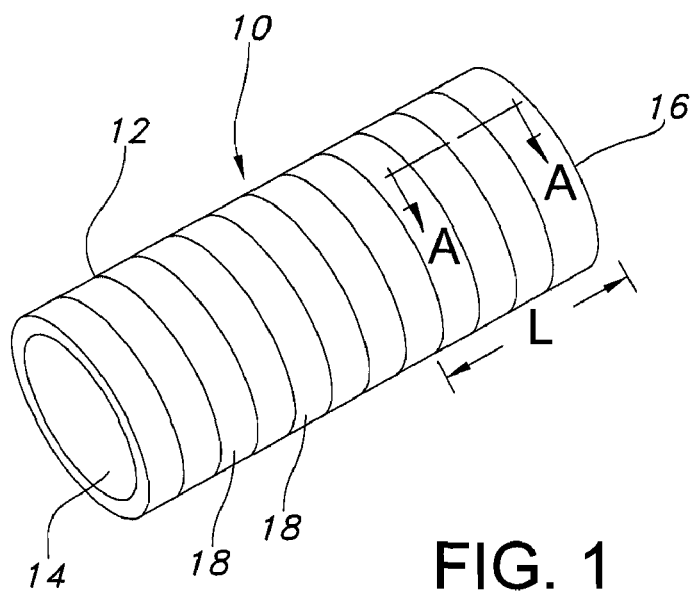
FIG. 1 is a perspective view of a stent embodiment having a plurality of wound stent elements forming a closed-wall structure according to the present invention.
Figure 2:
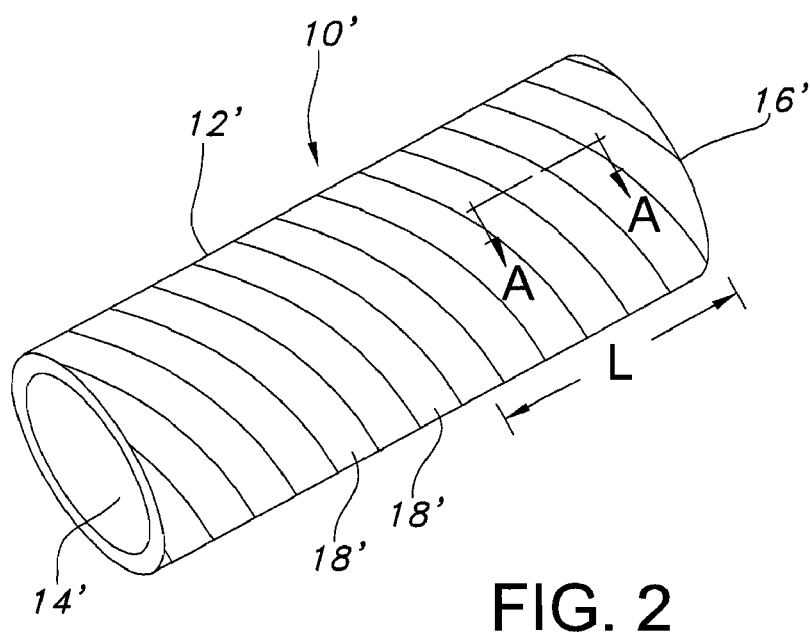
FIG. 2 is a perspective view of another stent embodiment having a plurality of wound stent elements forming a closed-wall structure according to the present invention.

FIG. 1 is a perspective view of stent 10 of the present invention. Stent 10 is a tubular structure having a wall 12 and opposed open ends 14, 16. The stent wall 12 may be formed from a plurality of helically wound elongate members 18 to form the cylindrical wall 12. The elongate members may be helically wound in a circular or a substantially circular fashion as depicted in FIG. 1. In such a winding the elongate members 18 may be wound in a perpendicular orientation or substantially perpendicular orientation to a longitudinal axis "L" of the stent 10. Alternatively, or in addition to, the elongate members 18' may be helically wound in an oblique fashion as depicted in FIG. 2 to form the tubular wall 12' of stent 10'. In such a winding the elongate members 18' may be wound in an obliquely acute or obtuse orientation to a longitudinal axis "L" of the stent 10'. Although the elongate strands 18, 18' are depicted as being parallel or substantially parallel to each other in FIGS. 1 and 2, the present invention, however, is not so limited. For example, the elongate strands 18, 18' may be skewed of helically wound at a varying angle along the longitudinal axis "L" over the longitudinal expanse of the stent 18, 18' or over a portion of the longitudinal expanse of the stent 18, 18'.

Figure 3:
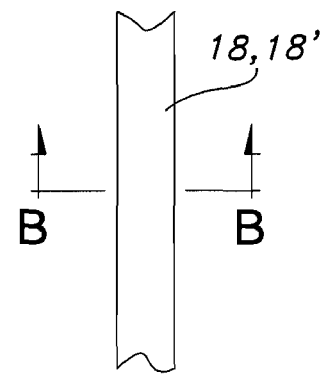
FIG. 3 is a top planar view of one of the stent elements of FIGS. 1 and/or 2.
Figure 4:
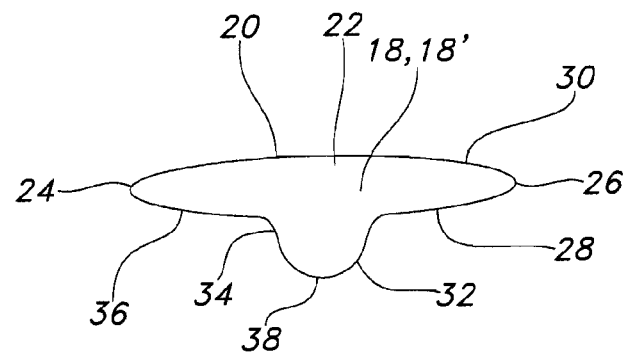
FIG. 4 is a cross-sectional view of the stent element of FIG. 3.

FIG. 3 is a top planar view of the elongate member 18, 18' of FIGS. 1 and/or 2 taken along the A-A axis. The size of the elongate member 18, 18', including length, width and/or height, may be any suitable size, including extremely small, as long as the stent of the stent 10, 10' remains sufficiently strong for its intended purpose. FIG. 4 is a cross-section view of the elongate member 18, 18' of FIG. 3 taken along the B-B axis. The elongate members 18, 18' include an upper flange or overlapping and/or intersecting portion 20 having a longitudinal extent 22 and opposed and convexly rounded sides 24, 26 defining a width of the members 18, 18' therein between. The elongate members 18, 18' further include opposed luminal and exterior surfaces 28, 30, respectively. The exterior surfaces 30 of the elongated members 18, 18' are desirably curved surfaces, in particular convexly curved surfaces. The present invention, however, is not so limited, and the exterior surfaces 30 of the elongated members 18, 18' may be planar, substantially planar, approximately planar, concavely curved, contoured, and the like. As used herein the term curved refers to a surface that is not planar or flat. A curved surface is one that includes at least three points having a radius of curvature. A substantially curved surface has a smaller radius of curvature while a relatively curved surface has larger radius of curvature. A non-limiting example of a relatively curved surface is one having a radius of curvature of about 10 cm to 50 cm, or larger. A non-limiting example of a substantially curved surface is one having a radius of curvature of about 10 cm, or smaller. The luminal surfaces 28 of the elongated members 18, 18' may further include a raised convexly arched, lobately shaped protuberance 32 or a plurality of protuberances 32 (not shown). The elongate members 18, 18' may be described as generally T-shaped members with rounded edges, more particularly a generally rounded T-shape with a flattened or reduced vertical portion and an extended horizontal portion. Desirably, the longitudinal extent 22 of the upper overlapping portion 20 between the opposed sides 24, 26 of the elongate members 18, 18' is larger than the longitudinal extent 34 from the base 36 of the luminal surfaces 28 to the peak 38 of the protuberance 32. The dimensions and materials of the elongate members 18, 18' are desirably chosen such that the stent wall 12, 12' is self-supporting without another support structure incorporated into or abutting the elongate members 18, 18'. The elongate members 18, 18' are desirably made from polymeric materials, more desirably shape memory polymeric materials, which materials may be molded, extruded, cast, and the like to form the elongate members 18, 18'. As used herein the terms "molded", "extruded" and/or "cast", and variants thereof, refer to materials not formed by weaving, braiding, knitting, filament winding, filament meshing of filaments or threads, including monofilament and multifilament strands of natural or synthetic materials, including polymeric and/or metallic filaments. Such molded, extruded, cast members 18, 18' of the present invention are typically unitary members.

Figure 5B:
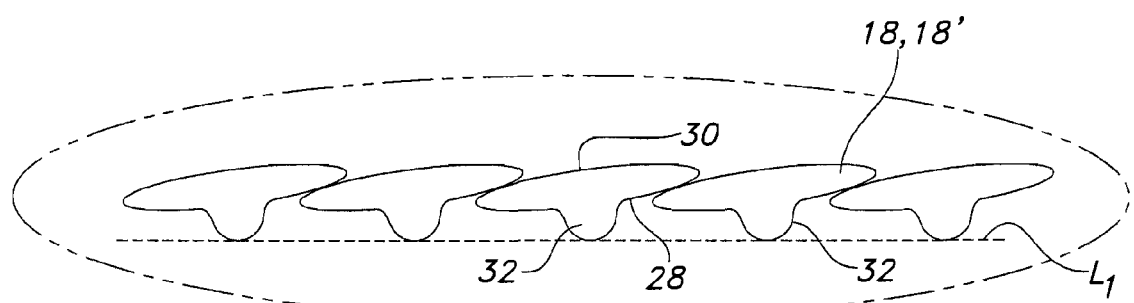
FIG. 5B is an exploded, cross-sectional view of a portion of an upper wall of the stent of FIG. 5A.
Figure 5A:
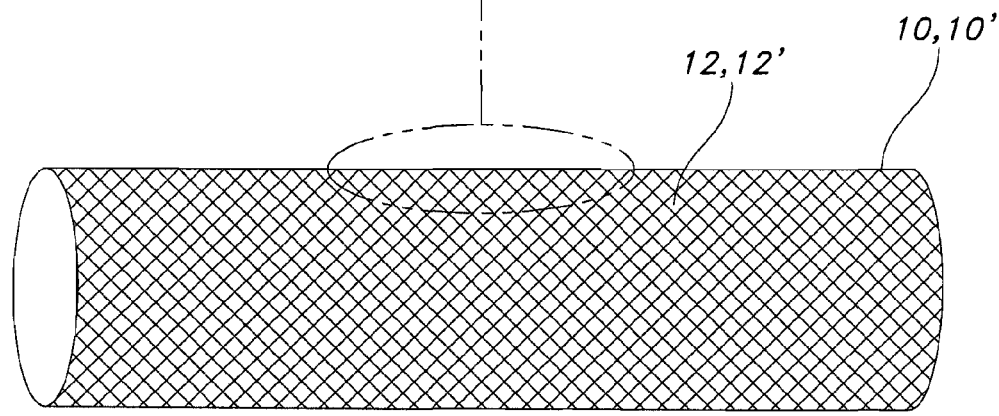
FIG. 5A is an illustration of the stent of the invention in a longitudinally straight state.

FIG. 5A is a schematic depiction of the stent 10, 10' in a straight or substantially straight orientation. FIG. 5B is an exploded cross-sectional view of a portion of the stent wall 12, 12' of FIG. 5A. As depicted in FIG. 5B, the exterior surface 30 of one elongate member 18, 18' overlaps the luminal surfaces 28 of an adjacent elongate member 18, 18'. In other words, the elongate members 18, 18' are juxtaposingly disposed in an overlapping fashion to define the stent wall 12, 12' of the stent 10, 10'. Desirably, the peaks 38 of the protuberances 32 are aligned or substantially aligned along a longitudinal axis "$L_1$" to define a somewhat smooth or substantially smooth luminal surface of the stent 10, 10'. Further, the longitudinal extent 34 of the protuberance 32 may be minimized to provide a smooth or substantially smooth luminal surface of the stent 10, 10'. As described below, the adjacent or juxtaposed elongate members 18, 18' are not securably attached to each other so that one elongate member 18, 18' may move with respect to an adjacent or proximal elongate members 18, 18'. As such, the elongate members 18, 18' are juxtaposingly disposed in a slidingly overlapping fashion or orientation.

Figure 6B:
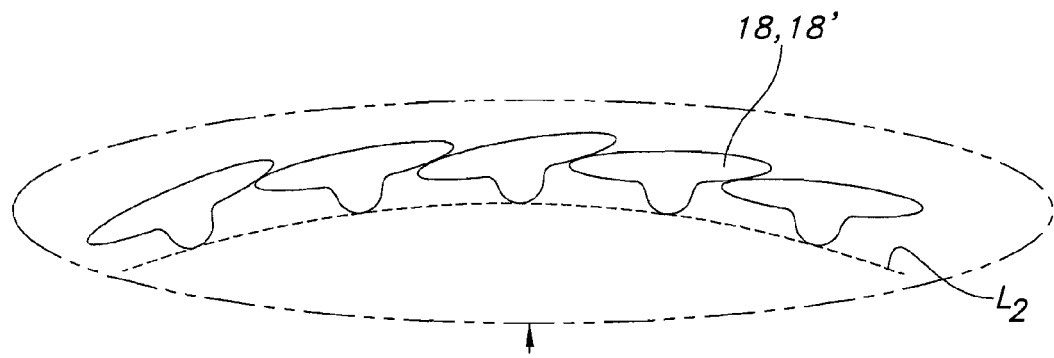
FIG. 6B is an exploded, cross-sectional view of a portion of an upper wall of the stent of FIG. 6A.
Figure 6A:
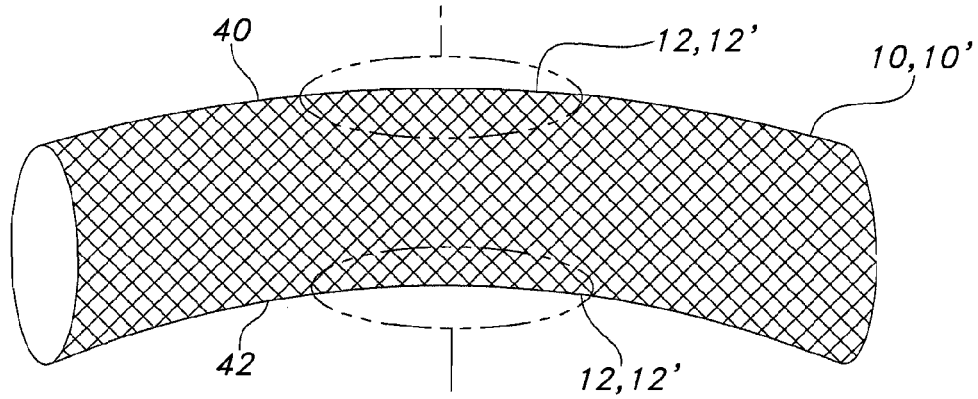
FIG. 6A is an illustration of the stent of the invention in a curved or flexed state.
Figure 6C:
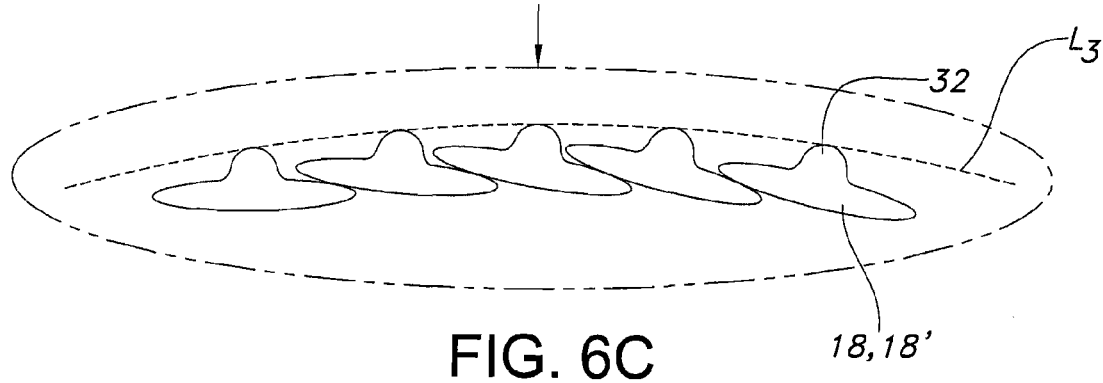
FIG. 6C is an exploded, cross-sectional view of a portion of a lower upper wall of the stent of FIG. 6A.

FIG. 6A is a schematic depiction of the stent 10, 10' in a curved state or orientation. FIG. 6B is an exploded cross-sectional view of an upper portion 40 of the stent wall 12, 12' of FIG. 6A. The upper portion 40 of the stent wall 12, 12' may be viewed or characterized as having a major radius of curvature "$L_2$". FIG. 6C is an exploded cross-sectional view of a lower portion 42 of the stent wall 12, 12' of FIG. 6A. The lower portion 42 of the stent wall 12, 12' may be viewed or characterized as having a minor radius of curvature "$L_3$". As depicted in FIGS. 6B and 6C, when the stent 10, 10' in a curved is bent or curved, the juxtaposed elongate members 18, 18' on the major radius of curvature "$L_2$" separate relative to one another, and the juxtaposed elongate members 18, 18' on the minor radius of curvature "$L_3$" collapse or move closer relative to one another. The protuberances 32 on the minor radius of curvature "$L_3$" may serve as a potential hindrance to the degree contraction or movement of one of elongate member 18, 18' to another elongate member 18, 18' on the minor radius of curvature "$L_3$". Alternatively, or in addition to, the longitudinal extent 34 of the protuberance 32 may also serve an additional engaging surface between juxtaposed elongate members 18, 18'.

The curved luminal and exterior surfaces 28, 30 provide for, among other things, increased areas or surfaces where the juxtaposed elongate members 18, 18' may abuttingly engage one and the other. This is especially evident for elongate members 18, 18' having convexly curved luminal and exterior surfaces 28, 30 and convexly rounded sides 24, 26. In contrast, juxtaposed and overlapping flat ribbons will have less engaging surface, especially when a stent made from such ribbons is in a curved or bent state. Further, gaps between the portions of the flat ribbons may increase as such a stent made from such ribbons is bent as the flat ribbons may tend to separate in a scissor-like fashion. Also in contrast to the present invention, a stent made from coiled wires or threads will not provide a substantially continuous stent surface as the coils or threads will simply separate on the major axis of curvature, thereby resulting in gaps between proximal coil or thread portions. In other words, the convexly curved luminal and exterior surfaces 28, 30 and convexly rounded sides 24, 26 of the elongate members 18, 18' maximize the abutting engagement of juxtaposed elongate members 18, 18' when the stent 10, 10' is bent or curved thereby providing no or only very small gaps in the wall 12, 12' of the stent 10, 10'. Stents with pronounced gaps provide areas for tumor in-growth thereat. Thus, the juxtaposed elongate members 18, 18' of the present invention minimize and/or prevent tumor in-growth and possible re-occlusion of the implanted stent 10, 10', especially when the stent 10, 10' is implanted in a curved portion of a bodily lumen.

Figure 7A:
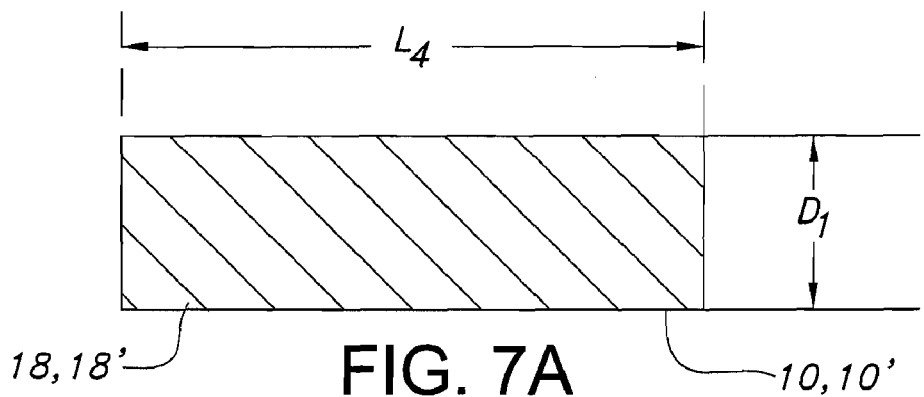
FIG. 7A is a planar view of an unexpanded or radially contracted stent of the present invention.
Figure 7B:
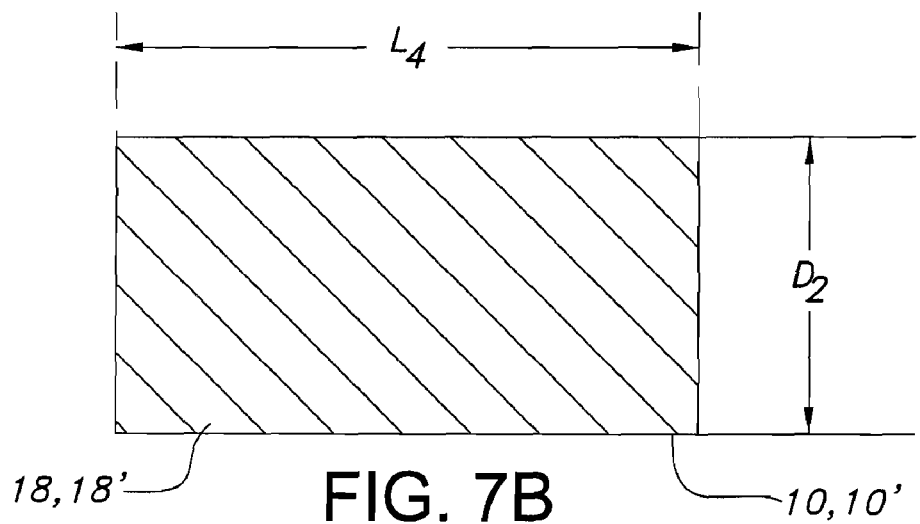
FIGS. 7B and 7C are planar views of the stent of FIG. 7A in radially expanded states.
Figure 7C:
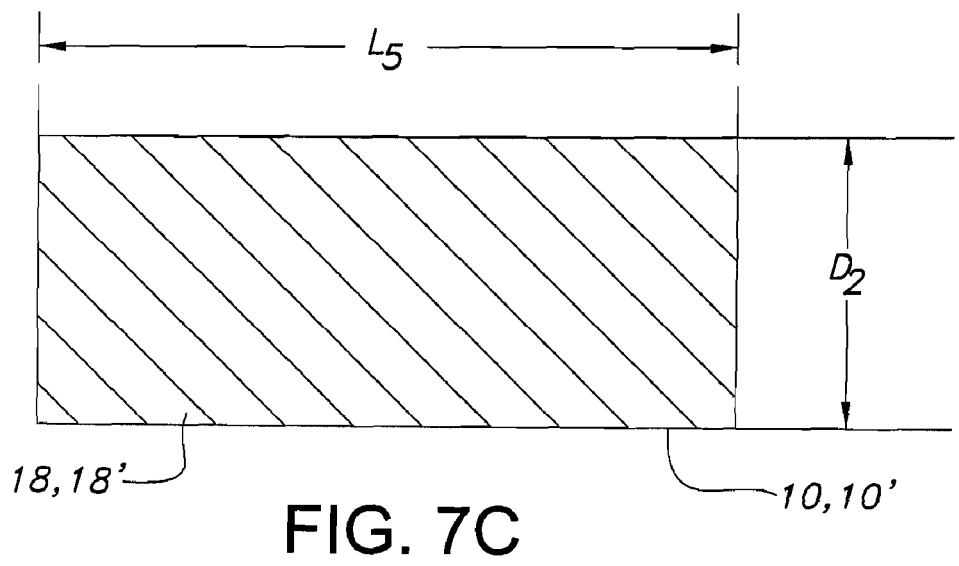

The curved luminal and exterior surfaces 28, 30 having large longitudinal extents 22 between the opposed sides 24, 26 of the elongate members 18, 18' also provide for, among other things, increased portions or surfaces where the juxtaposed elongate members 18, 18' may abuttingly engage one and the other when the stent 10, 10' is in its radially contracted and radially expanded states. Stents with just narrow abutting members in the contracted state may likely have gaps between the stent members in the expanded state and vice versa. Thus, the elongate members 18, 18' of the present invention provide for a closed or substantially fluid-tight stent wall 12, 12' in both a radially contracted and a radially expanded stent 10, 10'. For example, as depicted in FIG. 7A, the stent 10, 10' has a substantially continuous and closed stent wall 12, 12' which is free of gaps between proximal elongate members 18, 18'. The stent 10, 10' is also depicted in a radially contracted state in FIG. 7A. In a radially expanded state, as depicted in FIG. 7B where the diameter D2 of the expanded stent is greater than the diameter D1 of the contracted stent, the stent wall 12, 12' remains substantially continuous and closed, i.e., free of gaps between proximal elongate members 18,18'. Further, as depicted in FIGS. 7A and 7B, the longitudinal expanse "L4" of the stent 10, 10' may remain constant, substantially constant or relatively constant between the radially contracted and radially expanded states of the stent 10, 10'. The present invention, however, is not so limited, and as depicted in FIG. 7C the longitudinal expanse "L5" of the stent 10, 10' in the expanded state may be different from the longitudinal expanse "L4" of the contracted stent 10, 10'. While "L5" is depicted as being greater than "L4", the present invention is not so limited and "L5" may be shorter the "L4". In other words, the stent 10, 10' may have minimal change of its longitudinal expanse, may longitudinally foreshorten or longitudinally lengthen as it transforms between its radially expanded and radially contracted states.

As described above, the elongate members 18, 18' are desirably comprise, include or made from shape memory polymers or shape memory polymeric materials. Shape memory refers to the ability of a material to undergo structural phase transformation such that the material may define a first configuration under particular physical and/or chemical conditions, and to revert to an alternate configuration upon a change in those conditions. Stimulus for such a phase transformation may include, but is not limited to, temperature, pH, salinity, hydration, and others.

Shape memory polymers generally have hard segments and soft segments, which are relative terms relating to the transition temperature of the segments. As used herein, the term "segment" refers to a block or sequence of polymer forming part of the shape memory polymer. Generally speaking, hard segments have a higher glass transition temperature (Tg) than soft segments.

Useful natural polymer segments or polymers include, but are not limited to, proteins, such as casein, gelatin, gluten, zein, modified zein, serum albumin and collagen, polysaccharides, such as alginate, chitin, celluloses, dextrans, pullulane, and polyhyaluronic acid; poly(3-hydroxyalkanoate)s, poly(β-hydroxybutyrate), poly(3-hydroxyoctanoate) and poly(3-hydroxyfatty acids). Useful natural bioabsorbable or biodegradable polymer segments or polymers include polysaccharides such as alginate, dextran, cellulose, collagen and chemical derivatives thereof, and proteins such as albumin, zein and copolymers and blends thereof, alone or in combination with synthetic polymers. Suitable synthetic polymer blocks include polyphosphazenes, poly(vinyl alcohols), polyamides, polyester amides, poly(amino acid)s, synthetic poly(amino acids), polyanhydrides, polycarbonates, polyacrylates, polyalkylenes, polyacrylamides, polyalkylene glycols, polyalkylene oxides, polyalkylene terephthalates, polyortho esters, polyvinyl ethers, polyvinyl esters, polyvinyl halides, polyvinylpyrrolidone, polyesters, polylactides, polyglycolides, polysiloxanes, polyurethanes and copolymers thereof. Examples of suitable polyacrylates include poly(methyl methacrylate), poly(ethyl methacrylate), poly(butyl methacrylate), poly(isobutyl methacrylate), poly(hexyl methacrylate), poly(isodecyl methacrylate), poly(lauryl methacrylate), poly(phenyl methacrylate), poly(methyl acrylate), poly(isopropyl acrylate), poly(isobutyl acrylate) and poly(octadecyl acrylate). Synthetically modified natural polymers include cellulose derivatives such as alkyl celluloses, hydroxyalkyl celluloses, cellulose ethers, cellulose esters, nitrocelluloses, and chitosan. Examples of suitable cellulose derivatives include methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, arboxymethyl cellulose, cellulose triacetate and cellulose sulfate sodium salt. Examples of synthetic biodegradable polymer segments or polymers include polyhydroxy acids, such as polylactides, polyglycolides and copolymers thereof, poly(ethylene terephthalate); poly(hydroxybutyric acid); poly(hydroxyvaleric acid); poly[lactide-co-(ϵ-caprolactone)]; poly[glycolide-co-(ϵ-caprolactone)]; polycarbonates, poly(pseudo amino acids); poly(amino acids); poly(hydroxyalkanoate)s; polyanhydrides; polyortho esters; and blends and copolymers thereof. Rapidly biodegradable polymers such as poly(lactide-co-glycolide)s, polyanhydrides, and polyorthoesters, which have carboxylic groups exposed on the external surface as the smooth surface of the polymer erodes, can also be used. In addition, polymers containing labile bonds, such as polyanhydrides and polyesters, are well known for their hydrolytic reactivity. Their hydrolytic degradation rates can generally be altered by simple changes in the polymer backbone and their sequence structure. Examples of suitable hydrophilic polymers include, but are not limited to, poly(ethylene oxide), polyvinyl pyrrolidone, polyvinyl alcohol, poly(ethylene glycol), polyacrylamide poly(hydroxy alkyl methacrylates), poly(hydroxy ethyl methacrylate), hydrophilic polyurethanes, poly(hydroxy ethyl acrylate), hydroxy ethyl cellulose, hydroxy propyl cellulose, methoxylated pectin gels, agar, starches, modified starches, alginates, hydroxy ethyl carbohydrates and mixtures and copolymers thereof. Hydrogels may also be suitably be used and can be formed from polyethylene glycol, polyethylene oxide, polyvinyl alcohol, polyvinyl pyrrolidone, polyacrylates, poly(ethylene terephthalate), poly(vinyl acetate), and copolymers and blends thereof. Several polymeric segments, for example, acrylic acid, are elastomeric only when the polymer is hydrated and hydrogels are formed. Other polymeric segments, for example, methacrylic acid, are crystalline and capable of phase transition even when the polymers are not hydrated. Either type of polymeric block can be used, depending on the desired application and conditions of use. Additional details of useful shape memory polymeric compositions may be found in U.S. Pat. No. 6,887,266 to Williams et al., the contents of which are incorporated herein by reference.

One useful class of particularly useful shape memory polymers includes a class of (meth)acrylate compositions having a first (meth)acrylate monomer having a lower glass transition temperature (Tg), typically less than about 25° C., and a second (meth)acrylate monomer having a higher glass transition temperature (Tg), typically greater than about 25° C. These ranges of glass transition temperatures are, however, nonlimiting. Useful, but nonlimiting, first monomers include butyl (meth)acrylate, pentafluoropropylacrylate and combinations thereof. Useful, but nonlimiting, second monomers include methylmethacrylate, isobornyl methacrylate, isobutyl methacrylate, perfluoroacetylmethacrylate, tertiary butylmethacrylate, phenylethylmethacrylate, styrene, hydroxyethyl methacrylate, glycerol methacrylate, n-vinyl pyrrolidone, heptadecafluorodecyl methacrylate and combinations thereof. Such compositions may include a third of polyethyleneglycol dimethacrylate, polyethyleneglycol methacrylate, polyethyleneglycol acrylate and combinations thereof. Additional details of these compositions may be found in U.S. Pat. Nos. 7,115,691 to Alvarado et al., 5,603,722 to Phan et al. and 5,163,952 to Froix, the contents of which are incorporated herein by reference.

Further, the stent 10, 10' may be made from polymeric materials which may also include radiopaque materials, such as metallic-based powders or ceramic-based powders, particulates or pastes which may be incorporated into the polymeric material. For example, the radiopaque material may be blended with the polymer composition from which the polymeric wire is formed, and subsequently fashioned into the stent as described herein. Alternatively, the radiopaque material may be applied to the surface of the metal or polymer stent. Various radiopaque materials and their salts and derivatives may be used including, without limitation, bismuth, barium and its salts such as barium sulfate, tantalum, tungsten, gold, platinum and titanium, to name a few. Additional useful radiopaque materials may be found in U.S. Pat. No. 6,626,936, which is herein incorporated in its entirely by reference. Metallic complexes useful as radiopaque materials are also contemplated. The stent 10, 10' may be selectively made radiopaque at desired areas along the stent or made be fully radiopaque, depending on the desired end-product and application. Alternatively, the stent 10, 10' may also have improved external imaging under magnetic resonance imaging (MRI) and/or ultrasonic visualization techniques. MRI is produced by complex interactions of magnetic and radio frequency fields. Materials for enhancing MRI visibility include, but not be limited to, metal particles of gadolinium, iron, cobalt, nickel, dysprosium, dysprosium oxide, platinum, palladium, cobalt based alloys, iron based alloys, stainless steels, or other paramagnetic or ferromagnetic metals, gadolinium salts, gadolinium complexes, gadopentetate dimeglumine, compounds of copper, nickel, manganese, chromium, dysprosium and gadolinium. To enhance the visibility under ultrasonic visualization the stent 10, 10' of the present invention may include ultrasound resonant material, such as but not limited to gold. Other features, which may be included with the stent 10, 10' of the present invention, include radiopaque markers; surface modification for ultrasound, cell growth or therapeutic agent delivery; varying stiffness of the stent or stent components; varying geometry, such as tapering, flaring, bifurcation and the like; varying material; varying geometry of stent components, for example tapered stent filaments; and the like.

Moreover, the stent 10, 10' of the present invention is not limited to the T-shaped members 18, 18' as depicted in, for example, FIG. 4, and the stent 10, 10' may comprise any suitably shaped member 18, 18'. Nonlimiting examples of such suitably shaped member 18, 18' include those described below in conjunction with FIGS. 8-22B.

Figure 8:
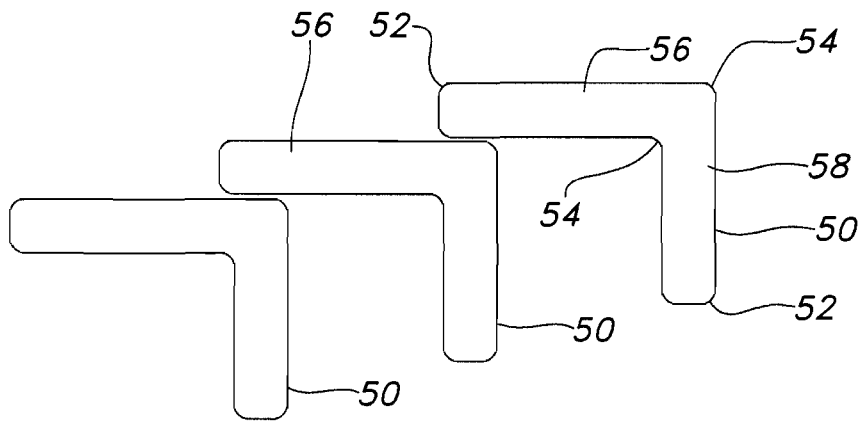
FIG. 8 is a cross-sectional view of another embodiment of stent elements of FIGS. 1 and/or 2 having an L-shape.

FIG. 8 depicts L-shaped stent members 50 which may comprise stent 10, 10' of the present invention. Desirably, the L-shaped members 50 may include rounded, somewhat rounded, or curved end portions 52 and/or rounded, somewhat rounded, or curved portions 54 where the one leg 56 of the L-shaped member 50 meets the other leg 58 of the L-shaped member 50. Further, the length and/or width of the legs 56, 58 may be the same or different. For example, the length of leg 56 may be larger than the length of leg 58 to provide a smooth or approximately smooth stent surface. Moreover, the L-shaped stent members 50 may comprise shape memory polymer and/or non-shape memory polymer, including portions comprising shape memory polymer and other portions not including shape memory polymer. Further, different portions of the L-shaped stent members 50 may comprise different shape memory polymers. Also, one member 50 may comprise shape memory polymer while another member 50 may not comprise shape memory polymer. Desirably, one leg 56 of the L-shaped member 50 is slidingly disposed about a portion of another leg 56 which provides, among other things, flexibility and/or movement of the legs 56 as the shape memory polymer grows.

Figure 9:
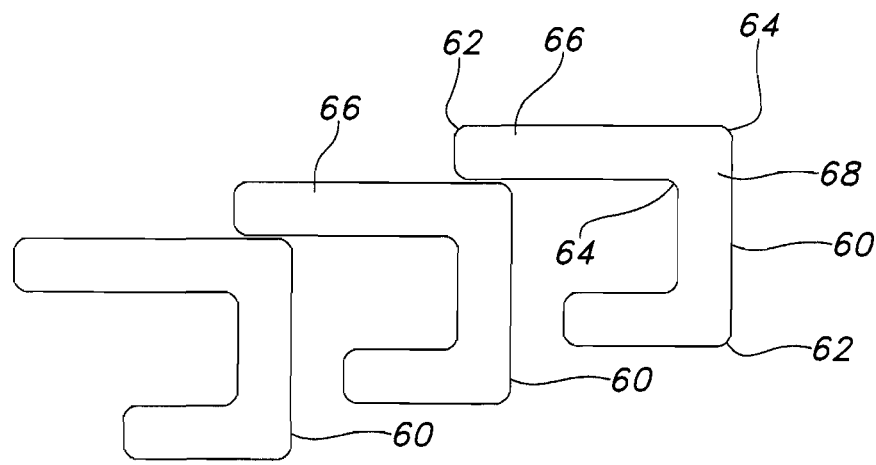
FIG. 9 is a cross-sectional view of another embodiment of stent elements of FIGS. 1 and/or 2 having a C-shape.

FIG. 9 depicts C-shaped stent members 60 which may comprise stent 10, 10' of the present invention. Desirably, the C-shaped members 60 may include rounded, somewhat rounded, or curved end portions 62 and/or rounded, somewhat rounded, or curved portions 64 where the one portion 66 of the C-shaped member 50 meets the other portion 68 of the C-shaped member 60. Further, the length and/or width of the portions 66, 68 may be the same or different. For example, as depicted in FIG. 9, the length of portion 66 may be larger than the length of portion 68 to provide a smooth or approximately smooth stent surface. Further, the portions 66, 68 may be symmetric, approximately symmetric, asymmetric, approximately asymmetric, and the like. Moreover, the C-shaped stent members 60 may comprise shape memory polymer and/or non-shape memory polymer, including portions comprising shape memory polymer and other portions not including shape memory polymer. Further, different portions of the C-shaped stent members 60 may comprise different shape memory polymers. Also, one member 60 may comprise shape memory polymer while another member 60 may not comprise shape memory polymer. Desirably, one portion 66 of the C-shaped member 60 is slidingly disposed about a portion of another portion 66 which provides, among other things, flexibility and/or movement of the portions 66 as the shape memory polymer grows.

Figure 10:
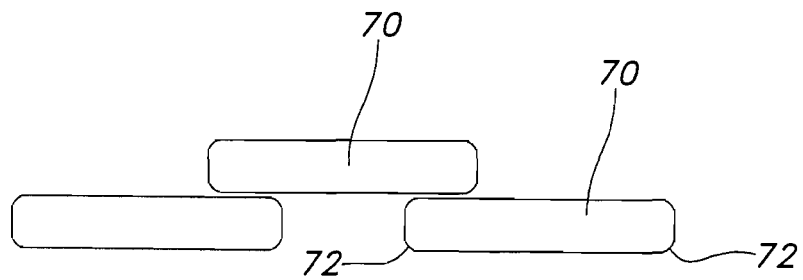
FIG. 10 is a cross-sectional view of another embodiment of stent elements of FIGS. 1 and/or 2 having an overlapping flat or ribbon shape.

FIG. 10 depicts overlapping flat or ribbon shaped stent members 70 which may comprise stent 10, 10' of the present invention. Desirably, the flat-shaped members 70 may include rounded, somewhat rounded, or curved end portions 72. Further, the length and/or width of the flat-shaped members 70 may be the same or different. The flat-shaped members 70 may comprise shape memory polymer and/or non-shape memory polymer, including portions comprising shape memory polymer and other portions not including shape memory polymer. Further, different portions of the flat-shaped members 70 may comprise different shape memory polymers. Also, one member 70 may comprise shape memory polymer while another member 70 may not comprise shape memory polymer. Desirably, one member 70 is slidingly disposed about a portion of another member 70 which provides, among other things, flexibility and/or movement of the members 70 as the shape memory polymer grows.

Figure 11:
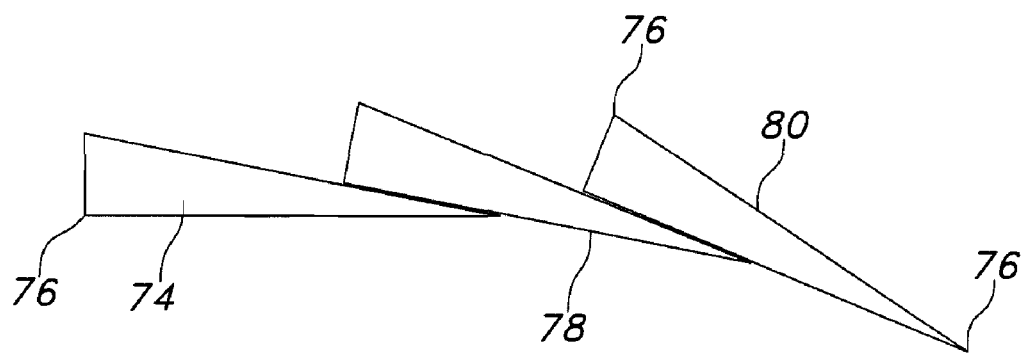
FIG. 11 is a cross-sectional view of another embodiment of stent elements of FIGS. 1 and/or 2 having a wedge shape where a flat surface of one element is juxtaposingly disposed to a tapered surface of an adjacent element.
Figure 12:
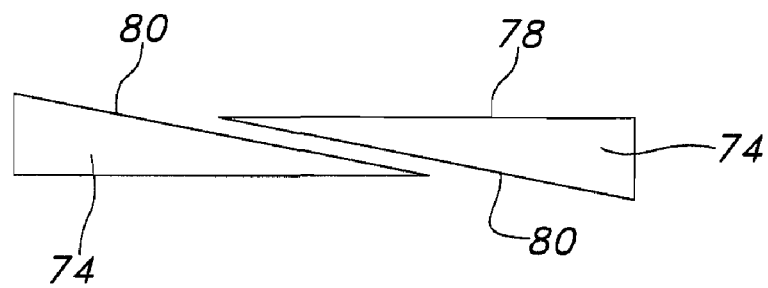
FIG. 12 is a cross-sectional view of an alternate embodiment of wedge-shaped stent elements of FIG. 11 having a where a tapered surface of one element is juxtaposingly disposed to a tapered surface of an adjacent element.

FIG. 11 depicts overlapping wedge-shaped stent members 74 which may comprise stent 10, 10' of the present invention. Desirably, the overlapping wedge-shaped stent members 74 may include rounded, somewhat rounded, or curved end portions 76. As depicted in FIG. 11, a flat or planar, including somewhat flat or planar, approximately flat or planar, and the like, portion 78 of one member 74 is proximal or juxtaposingly disposed to a tapered portion 80 on another member 74. As used herein, the term planar refers to a flat or essentially flat surface. A flat or relatively surface is one that is defined by a two-dimensional plane where all the points of the surface are within about five degrees or less from an axis defining the plane. A substantially flat surface is one that is defined by a two-dimensional plane where all the points of the surface are within about two degrees or less from an axis defining the plane. A surface which is not planar may be described as a non-planar or curved surface. Further, the length and/or width of the overlapping wedge-shaped stent members 74 may be the same or different. The overlapping wedge-shaped stent members 74 may comprise shape memory polymer and/or non-shape memory polymer, including portions comprising shape memory polymer and other portions not including shape memory polymer. Further, different portions of the overlapping wedge-shaped stent members 74 may comprise different shape memory polymers. Also, one member 74 may comprise shape memory polymer while another member 74 may not comprise shape memory polymer. Desirably, one member 74 is slidingly disposed about a portion of another member 74 which provides, among other things, flexibility and/or movement of the members 74 as the shape memory polymer grows. The present invention, however, is not limited to the slidably arrangement of the overlapping wedge-shaped stent members 74 as depicted in FIG. 11. For example, as depicted in FIG. 12, overlapping wedge-shaped stent members 74 may be provided where the tapered portion 80 of one member 74 is proximal or juxtaposingly disposed to the tapered portion 80 on another member 74.

Figure 13:
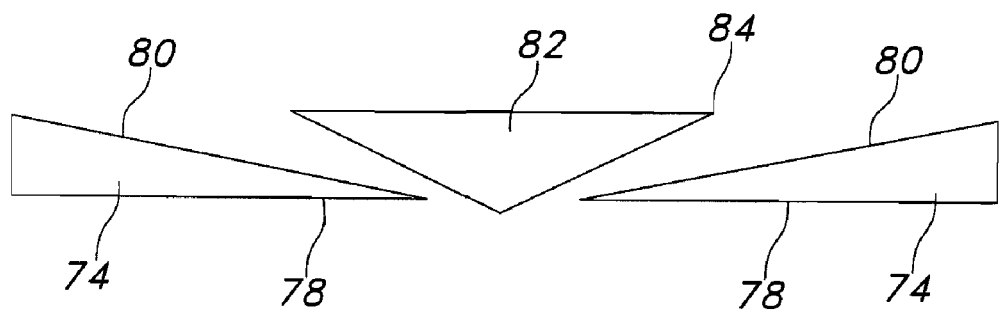
FIG. 13 is a cross-sectional view of an alternate embodiment of wedge-shaped stent elements of FIG. 11 having an overlapping triangularly shaped member juxtaposingly disposed between wedge-shaped members.

Further, as depicted in FIG. 13, a triangularly shaped stent member 82 may be slidingly disposed over wedge-shaped stent members 74. As depicted in FIG. 13, the triangularly shaped stent member 82 may be slidingly disposed about portions of the tapered portions 80 of the wedge-shaped stent members 74. Desirably, the triangularly shaped stent member 82 may include rounded, somewhat rounded, or curved end portions 84. The triangularly shaped stent member 82 may comprise shape memory polymer and/or non-shape memory polymer, including portions comprising shape memory polymer and other portions not including shape memory polymer. Further, different portions of the triangularly shaped stent member 82 may comprise different shape memory polymers.

FIGS. 14A and 14B depict convexly downward curved shaped stent members 84, 84' which may comprise stent 10, 10' of the present invention. Desirably, the curved members 84, 84' may include rounded, somewhat rounded, or curved end portions 86. As depicted in FIG. 14A, a side portion 88 proximal to the end portion 86 of one curved member 84, 84' may be juxtaposingly disposed toward a side portion 88 proximal to the end portion 86 of another curved member 84, 84'. Further, the curved members 84, 84' may be symmetric, approximately symmetric, asymmetric, approximately asymmetric, and the like. Further, the length and/or width of one curved member 84, 84' may be the same or different as the length and/or width of another curved member 84, 84'. Moreover, the L-shaped stent members 50 may comprise shape memory polymer and/or non-shape memory polymer, including portions comprising shape memory polymer and other portions not including shape memory polymer. Further, different portions of the curved members 84, 84' may comprise different shape memory polymers. Also, one curved member 84, 84' may comprise shape memory polymer while another curved member 84, 84' may not comprise shape memory polymer. As depicted in FIG. 14B, the curved members 84' become elongated and less curved after expansion or growth of shape memory polymer as compared to the curved members 84 depicted in FIG. 14A. As depicted in FIG. 14B, the end portion 86 of one curved member 84' may be juxtaposingly disposed and/or abutting the end portion 86 of another curved member 84'. The present, however, is not so limited, and the side portion 88 of one curved member 84' may be juxtaposingly disposed and/or abutting the side portion 88 of another curved member 84' (not shown).

FIGS. 15A and 15B depict arched shaped, desirably downwardly orientated, stent members 90, 90' which may comprise stent 10, 10' of the present invention. Desirably, the arched members 90, 90' may include rounded, somewhat rounded, or curved end portions 92 and/or rounded, somewhat rounded, or curved portions 94 where the one leg 98 of the arched shaped member 90, 90' meets the other leg 100 of the arched shaped member 90, 90'. As depicted in FIG. 15A, a side portion 96 proximal to the end portion 92 of one arched member 90, 90' may be juxtaposingly disposed toward a side portion 96 proximal to the end portion 92 of another arched member 90, 90'. Further, the arched members 90, 90' may be symmetric, approximately symmetric, asymmetric, approximately asymmetric, and the like. Further, the length and/or width of one arched member 90, 90' may be the same or different as the length and/or width of another arched member 90, 90'. Moreover, the arch-shaped stent members 90, 90' may comprise shape memory polymer and/or non-shape memory polymer, including portions comprising shape memory polymer and other portions not including shape memory polymer. Further, different portions of the arched members 90, 90' may comprise different shape memory polymers. Also, one arched member 90, 90' may comprise shape memory polymer while another arched member 90, 90' may not comprise shape memory polymer. As depicted in FIG. 15B, the arched members 90' become elongated and less curved after expansion or growth of shape memory polymer as compared to the arched members 90 depicted in FIG. 15A. As depicted in FIG. 15B, the end portion 92 of one arched member 90' may be juxtaposingly disposed and/or abutting the end portion 92 of another arched member 90'. The present, however, is not so limited, and the side portion 96 of one arched member 90' may be juxtaposingly disposed and/or abutting the side portion 96 of another arched member 90'.

FIG. 16A depicts round or circle shaped stent members 102 which may comprise stent 10, 10' of the present invention. As depicted in FIG. 16A, one stent member 102 may be juxtaposingly disposed, including in an abutting relationship, toward another stent member 102. Further, the width of one member 102 may be the same or different as the width of another member 102. Moreover, the stent members 102 may comprise shape memory polymer and/or non-shape memory polymer, including portions comprising shape memory polymer and other portions not including shape memory polymer. Further, different portions of the stent members 102 may comprise different shape memory polymers. Also, one member 102 may comprise shape memory polymer while another member 102 may not comprise shape memory polymer. As depicted in FIG. 16B, the members 102' become elongated into an oval shape after expansion or growth of shape memory polymer as compared to the members 102 depicted in FIG. 16A.

Figure 17:
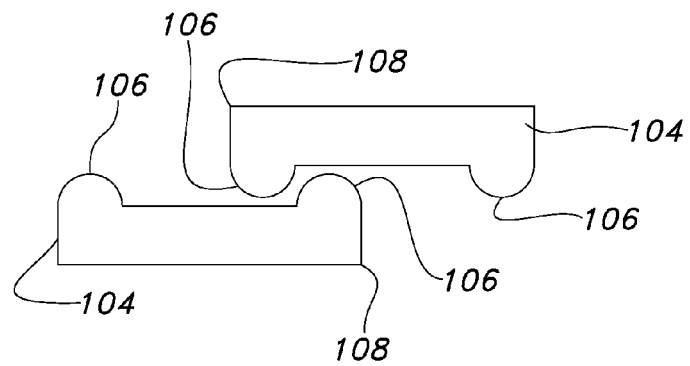
FIG. 17 is a cross-sectional view of another embodiment of stent elements of FIGS. 1 and/or 2 having an elongate ribbon shape with stops to limit sliding as the shape memory polymer extends.

FIG. 17 depicts overlapping flat or ribbon shaped stent members 104 which may comprise stent 10, 10' of the present invention. Desirably, the flat-shaped members 104 may include rounded, somewhat rounded, or curved end portions 108. Further, the length and/or width of the flat-shaped members 104 may be the same or different. As depicted in FIG. 17, the flat-shaped members 104 may include protuberances 106. The protuberances 106 may limit the degree of relative movement, for example, sliding among the flat-shaped members 104. Further, the flat-shaped members 104 are not limited to the protuberances 106 as depicted in FIG. 17, and other shaped detents may suitably be used as a stop to limit movement of the flat-shaped members 104. For example, one of the flat-shaped members 104 may have an inwardly directed detent, such as a notch, (not shown) which may be engage a protuberance 106 of a juxtaposed member 104. The flat-shaped members 104 may comprise shape memory polymer and/or non-shape memory polymer, including portions comprising shape memory polymer and other portions not including shape memory polymer. Further, different portions of the flat-shaped members 104 may comprise different shape memory polymers. Also, one member 104 may comprise shape memory polymer while another member 104 may not comprise shape memory polymer. Desirably, one member 104 is slidingly disposed about a portion of another member 104 which provides, among other things, flexibility and/or movement of the members 104 as the shape memory polymer grows.

Figure 18:
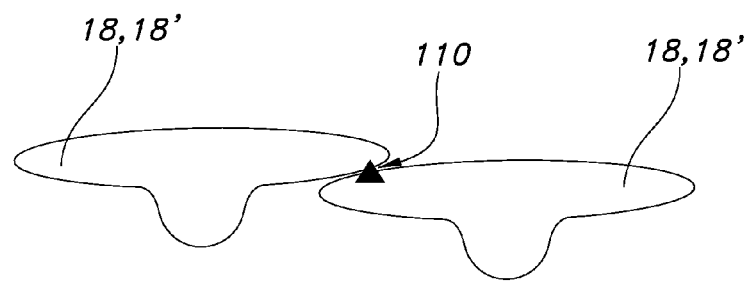
FIG. 18 is a cross-sectional view of another embodiment of stent elements of FIG. 4 having a stop to limit sliding as the shape memory polymer extends.

The present invention, however, is not limited to use of movement-limiting stops, detents or protuberances with just the flat-shaped members 104. Movement-limiting stops, detents or protuberances may suitably be used with any the stent forming members described herein. For example, as depicted in FIG. 18, T-shaped stent members 18, 18' may include a detent 110 to limit, minimize and/or control movement, for example a sliding movement, between the T-shaped stent members 18, 18'.

Figure 19:
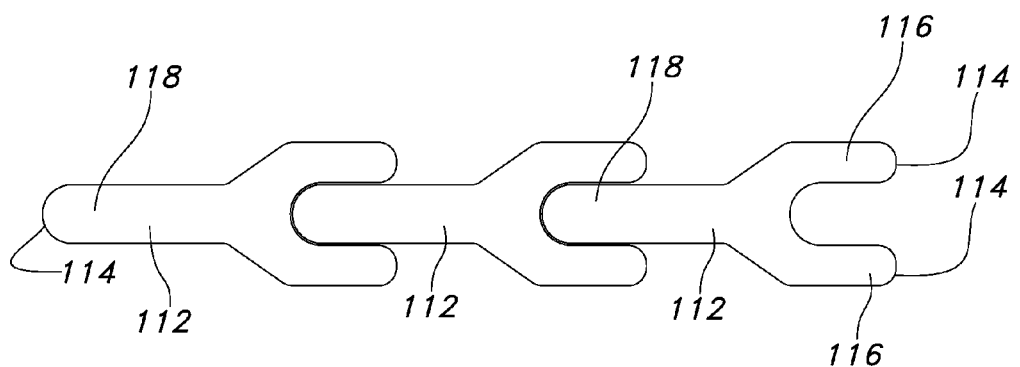
FIG. 19 is a cross-sectional view of another embodiment of stent elements of FIGS. 1 and/or 2 having a forked shape to interlock adjacent stent members.

FIG. 19 depicts overlapping fork-shaped stent members 112 which may comprise stent 10, 10' of the present invention. Desirably, the fork-shaped members 112 may include rounded, somewhat rounded, or curved end portions 114. Further, the length and/or width of the fork-shaped members 112 may be the same or different. As depicted in FIG. 19, the fork-shaped members 112 include a parted member 116 at one end and a non-parted member 118 at the opposed opposite end. The non-parted member 118 of one member 112 may be slidably disposed within a parted member 116 of an adjacent member 112. The present invention, however, is not limited to the use of fork-shaped members 112 having only one parted member 116. For example, some or all of the fork-shaped members 112 may have more than one parted member 116, for example two opposed parted member 116. The fork-shaped members 112 may limit the degree of relative movement, for example, sliding among the fork-shaped members 112, and may further serve to interlock juxtaposed fork-shaped members 112 to one and the other. The fork-shaped members 112 may comprise shape memory polymer and/or non-shape memory polymer, including portions comprising shape memory polymer and other portions not including shape memory polymer. Further, different portions of the fork-shaped members 112 may comprise different shape memory polymers. Also, one member 112 may comprise shape memory polymer while another member 112 may not comprise shape memory polymer.

Figure 20:
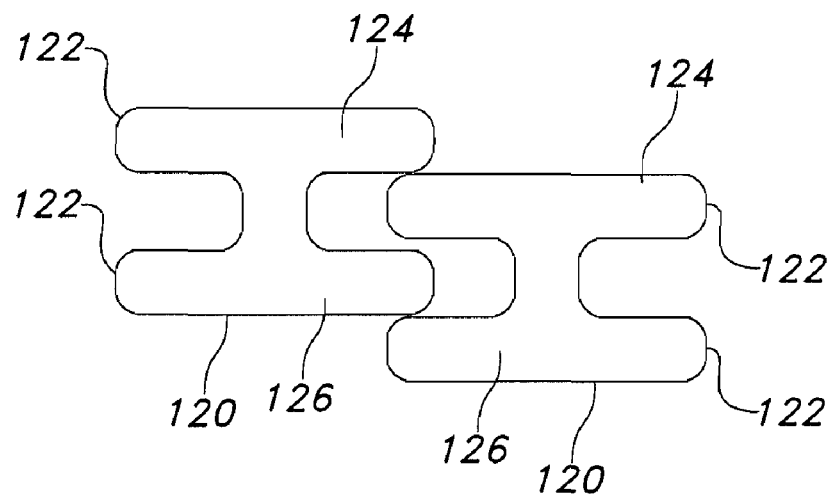
FIG. 20 is a cross-sectional view of another embodiment of stent elements of FIGS. 1 and/or 2 having an I-beam shape.

FIG. 20 depicts overlapping I-beam-shaped stent members 120 which may comprise stent 10, 10' of the present invention. Desirably, the I-beam-shaped members 120 may include rounded, somewhat rounded, or curved end portions 122. Further, the length and/or width of the I-beam-shaped members 120 may be the same or different. As depicted in FIG. 20, the I-beam-shaped members 120 include an upper portion 124 and a lower portion 126. The upper portion of one member 120 may be slidably disposed along the upper portion 124 of a proximal or adjacent member 120. Additionally or alternatively, the lower portion 126 of one member 120 may be slidably disposed along the lower portion 126 of a proximal or adjacent member 120. I-beam-shaped members 120 may comprise shape memory polymer and/or non-shape memory polymer, including portions comprising shape memory polymer and other portions not including shape memory polymer. Further, different portions of the I-beam-shaped members 120 may comprise different shape memory polymers. Also, one member 120 may comprise shape memory polymer while another member 120 may not comprise shape memory polymer.

Figure 21A:
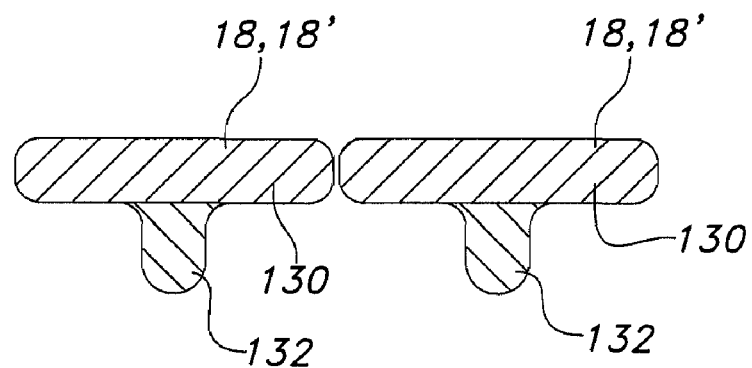
FIG. 21A is a cross-sectional view of another embodiment of stent elements of FIG. 4 where the portions of the elements comprise shape memory polymer and n-n-shape memory polymer.
Figure 21B:
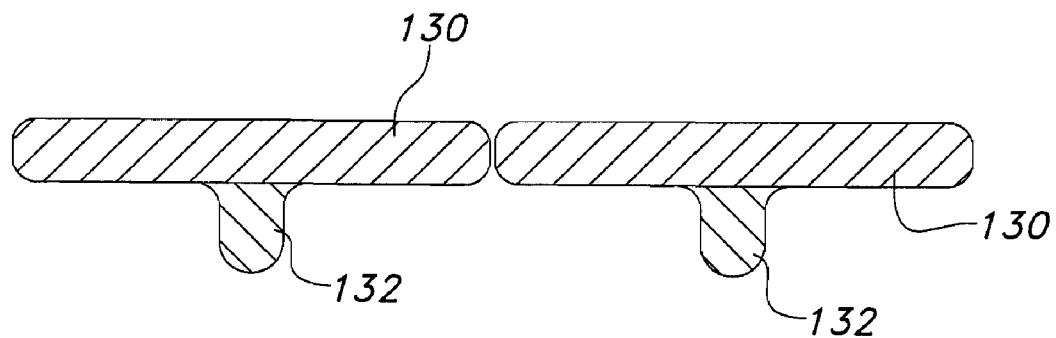
FIG. 21B is a cross-sectional view of the elements of FIG. 21A after shape memory polymer extends depicting an elongated shape memory portion.

As depicted in FIGS. 21A and 21B, the T-shaped members 18, 18' may include a portion 130 comprising shape memory polymer and a portion 132 not comprising shape memory polymer. In such a case, the shape memory portion 130 may expand or grow, as depicted in FIG. 21B, while the other portion 132 may not expand, grow or otherwise undergo substantial dimensional change. In such a manner, the dimensions of the stent 10, 10' may be controlled. For example, without growth or expansion of portion 132 a smoother stent surface may result as compared to a similar stent member having a similar portion capable of growth or expansion.

Figure 22A:
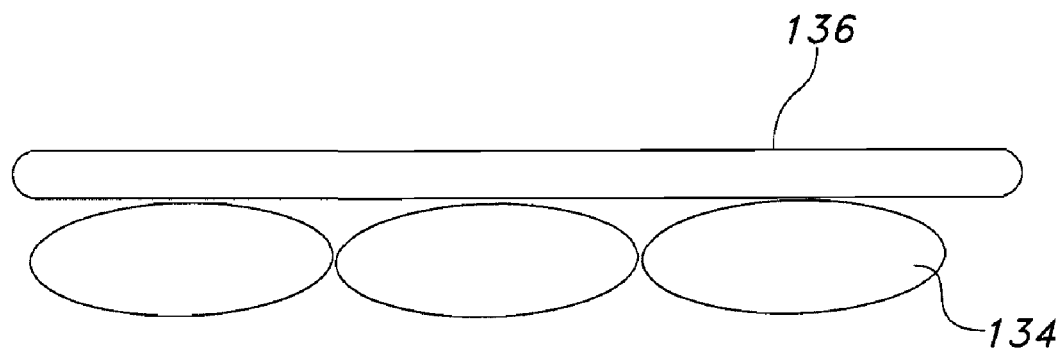
FIG. 22A is a cross-sectional view of the oval shaped elements having a covering over the exterior surface of the elements.
Figure 22B:
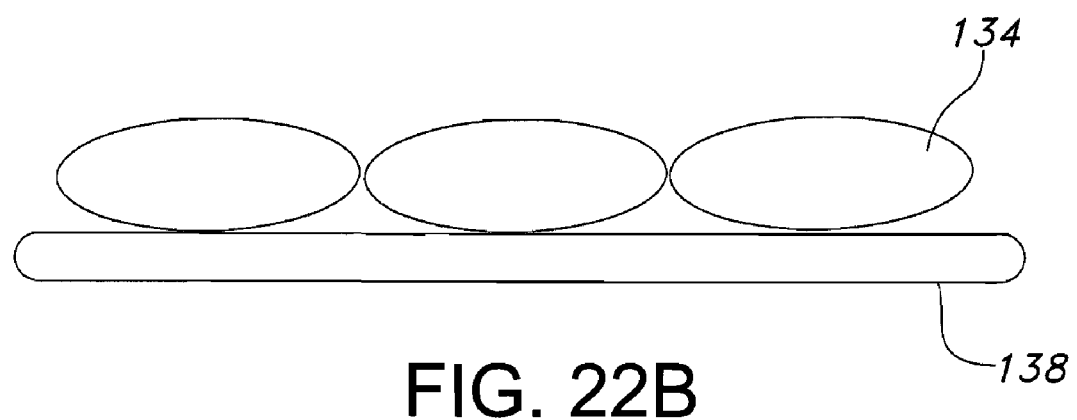
FIG. 22B is a cross-sectional view of the oval shaped elements having a liner over the interior surface of the elements.
Figure 22C:
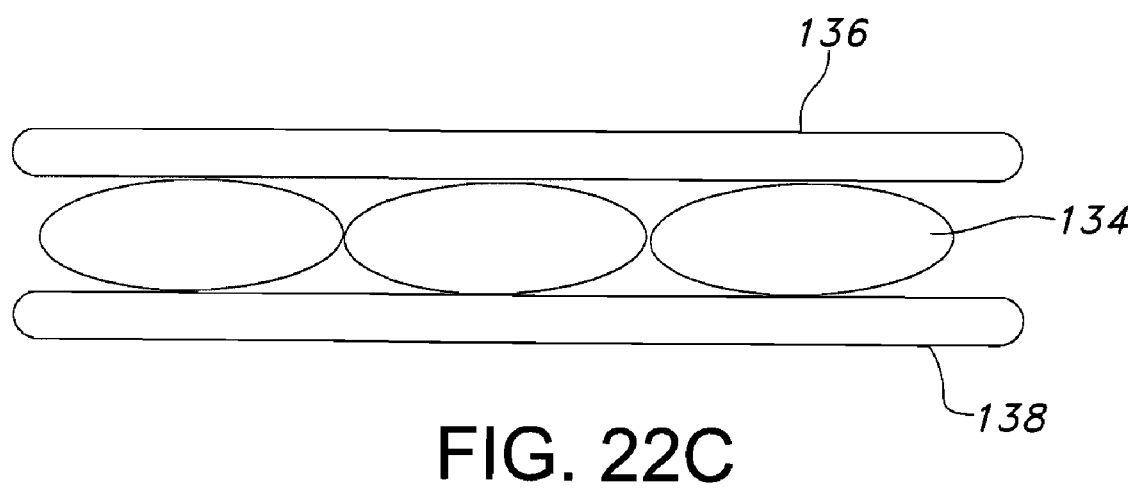
FIG. 22C is a cross-sectional view of the oval shaped elements having a covering over the exterior surface of the elements and a liner over the interior surface of the elements.

As depicted in FIGS. 22A-22C, stent members of the present invention may include an outer covering 136, an inner liner 138 or a combination thereof. Although an oval stent member 134 is depicted in FIGS. 22A-22C, stent 10, 10' may include a covering 136 and/or liner 138 with any or all of the herein described stent members. Further, the stent 10, 10' may be fully covered or partially covered, i.e., having portions not covered, by the covering 136 and/or the liner 138. Suitable materials for the covering 136 and/or the liner 138 may include elastic or polymeric materials, including, silicone, biodegradable materials, non-biodegradable materials, shape memory materials. Further, the covering 136 and/or the liner 138 may be a coating on the stent 10, 10'. The covering 136 and/or the liner 138 may be may be in the form of a tubular structure, for example composed of polymeric material and/or silicone. The covering 136 and/or the liner 138 may also comprise any plastic or polymeric material, desirably a somewhat hard but flexible plastic or polymeric material. The covering 136 and/or the liner 138 may be transparent or translucent, desirably substantially or partially transparent. Furthermore, the covering 136 and/or the liner 138 may be constructed of any suitable biocompatible materials, such as, but not limited to, polymers and polymeric materials, including fillers such as metals, carbon fibers, glass fibers or ceramics. Useful covering and/or lining materials include, but are not limited, polyethylene, polypropylene, polyvinyl chloride, polytetrafluoroethylene, including expanded polytetrafluoroethylene (ePTFE), fluorinated ethylene propylene, fluorinated ethylene propylene, polyvinyl acetate, polystyrene, poly(ethylene terephthalate), naphthalene dicarboxylate derivatives, such as polyethylene naphthalate, polybutylene naphthalate, polytrimethylene naphthalate and trimethylenediol naphthalate, polyurethane, polyurea, silicone rubbers, polyamides, polyimides, polycarbonates, polyaldehydes, polyether ether ketone, natural rubbers, polyester copolymers, silicone, styrene-butadiene copolymers, polyethers, such as fully or partially halogenated polyethers, and copolymers and combinations thereof.

Further, the stent 10, 10' may be treated with a therapeutic agent or agents, such as, but not limited to, anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); antineoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

The stents or elements of the invention could also be incorporated into conventional stents, for example braided, wound or slotted metallic or polymeric stents. The stents or elements of the invention may for a portion of a stent wall with such conventional stents or may serve as a covering or lining, in art or in total, for such a conventional stent.

While various embodiments of the present invention are specifically illustrated and/or described herein, it will be appreciated that modifications and variations of the present invention may be effected by those skilled in the art without departing from the spirit and intended scope of the invention. Further, any of the embodiments or aspects of the invention as described in the claims or throughout the specification may be used with one and another without limitation.

What is claimed is:
1. An implantable, radially distensible stent comprising:
a plurality of helically wound elongate members, each member comprising an overlapping portion having a longitudinal extent, opposed and convexly rounded sides defining a width and opposed luminal and exterior surfaces; each member comprising shape memory polymer;
wherein one of the opposed sides of one elongate member slidingly overlaps one of the opposed sides of an adjacent elongate member to define the overlapping portion and to form a substantially fluid-tight and self-supporting wall structure of the stent.
2. The stent of claim 1, wherein the sides of the overlapping portion are free of substantially sharp edges.
3. The stent of claim 1, wherein the exterior surface of the elongate members forms an exterior portion of the wall structure of the stent; and further wherein the exterior surface of the elongated members comprises a planar surface.
4. The stent of claim 3, wherein the planar surface comprises a relatively planar surface.
5. The stent of claim 3, wherein the planar surface comprises a substantially planar surface.
6. The stent of claim 1, wherein the exterior surface of the elongate members forms an exterior portion of the wall structure of the stent; and further wherein the exterior surface of the elongated members comprises a curved surface.
7. The stent of claim 6, wherein the exterior surface of the elongated members comprises a convexly curved surface.
8. The stent of claim 6, wherein the curved surface comprises a relatively curved surface.
9. The stent of claim 8, wherein the exterior surface of the elongated members comprises a convexly curved surface.
10. The stent of claim 6, wherein the curved surface comprises a substantially curved surface.
11. The stent of claim 10, wherein the exterior surface of the elongated members comprises a convexly curved surface.

12. The stent of claim 1, wherein the luminal surface of the elongated members further comprises a raised convexly arched, lobately shaped protuberance.

13. The stent of claim 12, wherein the elongate members comprise T-shaped members with rounded edges.

14. The stent of claim 1, wherein the luminal surface and the exterior surface of the elongated members comprise a closed surface.

15. The stent of claim 14, wherein the closed surface is a substantially closed surface.

16. The stent of claim 1, wherein the elongate members are selected from the group consisting of T-shaped members, L-shaped members, C-shaped members, ribbon-shaped members, wedge-shaped members, triangular-shaped members, convexly downward curved members, arch-shaped members, fork-shaped members, I-beam-shaped members, round members, oval members and combinations thereof.

17. The stent of claim 1, wherein the wall structure of the stent is self-supporting without other support structure incorporated into or abutting the elongate members.

18. The stent of claim 1, wherein the shape memory polymer comprises biodegradable portions.

19. The stent of claim 1, wherein the elongate members are selected from the group consisting of molded members, extruded members, cast members and combinations thereof.

20. The stent of claim 19, wherein the elongate members are non-textile members.

21. The stent of claim 1, further comprising detents to limit sliding movement between overlapping elongate members.

22. The stent of claim 1, wherein the stent is radially distensible between a radially contracted state and a radially expanded state; and wherein the self-supporting wall structure of the stent is substantially fluid-tight in both the radially contracted and the radially expanded states of the stent.

23. An implantable stent consisting essentially of:
a plurality of helically wound, elongate members made of shape memory polymer;
wherein each member comprises an overlapping portion having a longitudinal extent, opposed and convexly rounded sides defining a width and opposed luminal and exterior surfaces; and
wherein one of the opposed sides of one elongate member slidingly overlaps one of the opposed sides of an adjacent elongate member to define the overlapping portion and to form a substantially fluid-tight and self-supporting wall structure of the stent.

24. The stent of claim 23, wherein the elongate members are selected from the group consisting of molded members, extruded members, cast members and combinations thereof.

25. The stent of claim 24, wherein the exterior surface of the elongate members form an exterior portion of the wall structure of the stent; and further wherein the exterior surface of the elongated member comprises a curved surface.

26. The stent of claim 25, wherein the exterior surface of the elongated members comprises a convexly curved surface.

27. The stent of claim 25, wherein the curved surface comprises a relatively curved surface.

28. The stent of claim 27, wherein the exterior surface of the elongated members comprises a convexly curved surface.

29. The stent of claim 25 wherein the curved surface comprises a substantially curved surface.

30. The stent of claim 29, wherein the exterior surface of the elongated members comprises a convexly curved surface.

31. The stent of claim 23, wherein the luminal surface of the elongated members further comprises a protuberance.

32. The stent of claim 31, wherein the protuberance comprises a raised convexly arched, lobately shaped protuberance.

33. The stent of claim 23, wherein the elongate members are selected from the group consisting of T-shaped members, L-shaped members, C-shaped members, ribbon-shaped members, wedge-shaped members, triangular-shaped members, convexly downward curved members, arch-shaped members, fork-shaped members, I-beam-shaped members, round members, oval members and combinations thereof.

34. The stent of claim 23, wherein the wall structure of the stent is self-supporting without other support structure incorporated into or abutting the elongate members.

35. The stent of claim 23, wherein the shape memory polymer comprises a biodegradable portion.

36. The stent of claim 23, wherein the stent is radially distensible between a radially contracted state and a radially expanded state; and wherein the self-supporting wall structure of the stent is substantially fluid-tight in both the radially contracted and the radially expanded states of the stent.

37. An implantable, radially distensible stent comprising:
a helically wound elongate T-shaped member having a first upper traverse extent and a second perpendicularly projecting extent;
wherein the first extent comprises opposed and convexly rounded sides defining a width of the first extent and opposed luminal and exterior surfaces;
wherein the second extent comprises a convexly arched, lobately shaped protuberance;
wherein the side of a portion of the first extent of the elongate member slidingly overlaps a portion of the luminal or exterior surface an adjacently juxtaposed portion of the elongate member to form a self-supporting wall structure of the stent
wherein the self-supporting wall structure does not have an open lattice wall structure.

38. The stent of claim 37, wherein the member comprises shape memory polymer.

39. The stent of claim 38, wherein the shape memory polymer comprises a biodegradable material.

40. The stent of claim 37, wherein the exterior surface of the first extent of the elongate member forms an exterior portion of the wall structure of the stent; and further wherein the exterior surface is a curved surface.

41. The stent of claim 40, wherein the exterior surface of the elongated member is a convexly curved surface.

42. The stent of claim 37, wherein the structure of the stent wall is self-supporting without other support structure incorporated into or abutting the elongate member.

43. The stent of claim 37, wherein the stent is radially distensible between a radially contracted state and a radially expanded state; and wherein the self-supporting wall structure of the stent is substantially fluid-tight in both the radially contracted and the radially expanded states of the stent.

* * * * *

UNITED STATES PATENT AND TRADEMARK OFFICE
CERTIFICATE OF CORRECTION

PATENT NO. : 8,372,138 B2  
APPLICATION NO. : 12/136147  
DATED : February 12, 2013  
INVENTOR(S) : Gary Jordan Page 1 of 1

It is certified that error appears in the above-identified patent and that said Letters Patent is hereby corrected as shown below:

In the Claims:

Column 18, Line 51-52, delete "structure of the stent wall" and insert --wall structure of the stent--.

Signed and Sealed this  
Seventh Day of May, 2013

Teresa Stanek Rea  
*Acting Director of the United States Patent and Trademark Office*